(12) United States Patent
Hernandez et al.

(10) Patent No.: US 6,723,526 B1
(45) Date of Patent: Apr. 20, 2004

(54) COMPOSITION FOR FORMING A DRIED LENS-SHAPED PELLET COMPRISING ALBUMIN, STARCH, MICROORGANISMS AND SUGAR AND/OR SALT

(75) Inventors: Jean-François Hernandez, Villeneuve d'Ascq (FR); Fabrice Paluszkiewicz, Lille (FR); Eric Oudart, Lambersart (FR)

(73) Assignee: Institut Pasteur de Lille, Lille (FR)

( * ) Notice: Subject to any disclaimer, the term of this patent is extended or adjusted under 35 U.S.C. 154(b) by 0 days.

(21) Appl. No.: 09/446,457

(22) PCT Filed: Jun. 24, 1998

(86) PCT No.: PCT/FR98/01335

§ 371 (c)(1), (2), (4) Date: May 4, 2000

(87) PCT Pub. No.: WO99/00485

PCT Pub. Date: Jan. 7, 1999

(30) Foreign Application Priority Data

Jun. 25, 1997 (FR) .............................. 97 07954

(51) Int. Cl.⁷ .............................. C12N 1/00; C12N 1/04; C12N 1/20; C12P 1/00; C12Q 1/02
(52) U.S. Cl. .......................... 435/29; 435/41; 435/243; 435/252.1; 435/254.1; 435/260; 435/822
(58) Field of Search ................................ 435/174, 178, 435/243, 822, 252.1, 29, 41, 254.1, 260

(56) References Cited

U.S. PATENT DOCUMENTS 3,567,585 A    3/1971   Bloch et al. ............... 435/29
3,942,969 A  * 3/1976   Carroll, Jr. et al. ............ 71/5
5,545,555 A    8/1996   Racioppi et al. ......... 435/253.6
6,190,591 B1 * 2/2001   van Lengerich ............ 264/141

FOREIGN PATENT DOCUMENTS

EP    0 346 545    12/1989
EP    0 515 237    11/1992
EP    0 569 623    11/1993

* cited by examiner

Primary Examiner—David M. Naff
Assistant Examiner—Deborah K. Ware
(74) Attorney, Agent, or Firm—Finnegan, Henderson, Farabow, Garrett & Dunner, L.L.P.

(57) ABSTRACT

A composition for forming a dried lens-shaped pellet and processes therefore, are provided. The composition comprises 20 to 40% by weight albumin, about 2 to 5% by weight starch, about 40 to 90% by weight of sugar and/or salt, and about $10^2$ to $10^{11}$ microorganisms per gram of the composition. The microorganisms include bacteria, viruses, yeasts, protozoa, and fungi. A process for producing the pellet includes mixing the microorganisms with the albumin and starch to form a mixture, reducing water activity of the mixture by adding the sugar and/or salt to the mixture, shaping the mixture into pellets and drying the pellets under vacuum and at a temperature lower than about $-10°$ C. Also a process for producing a suspension of microorganisms includes resuspending the pellet into a suitable medium. Further, other processes using the pellet include fermentation, reconstituting for purposes of testing, and preserving.

27 Claims, 12 Drawing Sheets

COMPOSITION FOR FORMING A DRIED LENS-SHAPED PELLET COMPRISING ALBUMIN, STARCH, MICROORGANISMS AND SUGAR AND/OR SALT

CROSS-REFERENCE TO RELATED APPLICATIONS

Not applicable.

STATEMENT REGARDING FEDERALLY SPONSORED RESEARCH

Not applicable.

REFERENCE TO SUBMISSION ON COMPACT DISC

Not applicable.

BACKGROUND OF THE INVENTION

1. Field of the Invention

The present invention relates to a composition for preserving determined and reproducible amounts of micro-organisms.

It relates further to lens-shaped pellets comprising such a composition.

It has also as an object a process for producing such pellets.

2. Description of Related Art

The presence of benzene in mineral water Perrier, Listeria in cheese or epizooty of bovine spongiform encephalopathy have made quite a stir. The companies in the field of water, foodstuffs or health, positioned in sensitive sectors, have customers quite attentive to the quality of the goods delivered to them. Thus, the prevention of crisis situations is vital. In fact, any incident, such as a contamination, may have serious consequences for companies (waste production, image degradation). Consequently the danger of a contamination is a major concern for the authorities who edict increasingly stronger national, European or international regulatory constraints in terms of microbiological safety and for the industries who establish quality assurance plans including in particular the search of critical contamination points in the processes.

Consequently quite a number of public or private laboratories carry out each year many thousands of chemical and microbiological analysis in the fields of foodstuffs, environment or health.

Inter-laboratory studies have clearly showed that the laboratories generally worked with quite a good precision, but important variations existed between the results obtained from different laboratories.

Thus, excess results may be observed in laboratories having badly adjusted stoves, whereas default results are observed in laboratories having culture media of a poor quality.

Such erroneous results may have an great economical impact upon public health. The excess results may lead to refuse wrongly a product batch, to programme unnecessarily sanitizing operations to improve a beach quality or to disturb people by prohibiting tap water consumption.

In contrast, default results may incur a risk for the consumers by authorizing sales of contaminated products, distribution of poorly disinfected water or bathe in polluted water.

To secure reliable measurements, the checking laboratories have been asked to be accredited. Initially such accreditation only defined obligations of means (qualified personnel, adapted rooms, maintenance of measurement apparatus, control of raw materials and writing of the analytical procedures). At the present time, it also requires obligations of results. Such a new requirement imposes the implementation of a quality system including internal controls and participation to inter-laboratory tests.

For controlling the analytical chains internally and organize inter-laboratory tests, it is imperative to use reference materials. Such reference materials must be stable in time and should allow to reconstitute homogenous control samples containing an exact amount of the product to be dosed.

In chemistry, such reference materials have been existing for many years. In contrast, in the microbiological field, it is particularly difficult to preserve exact amounts of micro-organisms. In fact, the number of micro-organisms may either increase, if the preservation media enables their multiplication during manufacture, transport or storage, or decrease, if they die during manufacture, transportation or storage or at the time of the reconstitution of the control sample before use.

Methods for preserving micro-organisms, such as lyophilization and cryoconservation, have been already described in the all. However, such methods lead upon the conditioning step to high mortality rates amongst the micro-organisms being preserved, and consequently do not allow to master accurately the final quality of the surviving micro-organisms.

Thus, two patents appealing to a rude freezing method in liquid nitrogen do not describe the preservation of bacteria or micro-organisms and do not address to the problem of the quantitative dosages.

U.S. Pat. No. 5,364,756 discloses a method of cryoconservation for eucalyote cells. A suspension of such cells is prepared in a buffer comprising cryoprotecting agents, and then the solution is nebulized with ultrasounds so as to form microdroplets that are rapidly cooled and dried.

U.S. Pat. No. 5,405,616 relates to the preservation of pharmacologically active molecules. The particles comprising such molecules are predominantly made of a skeleton-forming water-soluble hydrophilic macromolecule. Various proteins are mentioned, mainly proteins from vegetal origin.

Exact amounts of micro-organisms may be obtained from naturally or artificially contaminated samples. However, the preservation of such samples cannot go beyond 24 hours and requires a lower temperature than 10° C.

Exact amounts of various bacteria are also obtained after freezing in a medium containing serum and inositol (1993 Peterz and Steneryd, J. of Appl. Bacteriol., 74, 143–148) or skimmed milk (1994 Schijven, Havellaar and Bahar, Appl. And Environ. Microbiol., 60, 4160–4162). It seems however that such frozen bacterial suspensions are not stable beyond three months for the first type of preparation and one year for the second one. Moreover, they require very demanding transportation conditions (short deliveries and maintenance of the temperature below −70° C.). Finally their stability in case of successive thaw-freeze has not been demonstrated.

Presently only atomization manages to conciliate the preservation, stability and transportation constraints with the requirement of an exact amount of micro-organisms.

Suspensions of *Bacillus cereus* in concentrated milk atomized and encapsulated in gelatine have been used as reference materials after transportation at room temperature (Paul H. In't Veld, 1993, Int. J. of Food Microbiol., 20, 23–36).

However, such technique is difficult to be implemented, because it requires a dissolution of the gelatine in a reconstitution medium maintained a 37° C. Moreover, some species like Aeromonas hydrophila, Pseudomonas aeruginosa and Campylobacter jejuni cannot be preserved stably by atomization. Such a process is not recommended either for preserving respiratory tract pathogens being transmissible with aerosols like Legionella pneumophila. Finally the reference materials prepared by atomization have a high cost.

DESCRIPTION OF THE INVENTION

It appears thus from the art that no process was known which would be easy to be carried out and cheap allowing to preserve stably exact amounts of micro-organisms.

The Assignee has solved this problem by finding a particular composition being able to hold viability of micro-organisms.

The present invention thus relates to a composition for preserving predetermined and reproducible amounts of micro-organisms comprising in combination efficient amounts of at least one material being able to form the skeleton of lens-shaped pellets and at least one saturating material as well as micro-organisms.

For the present invention it is meant by reproducible amounts of micro-organisms variations of the ratio between two measurements comprised, in 95% of the cases, between 0.25 and 4, more preferably between 0.5 and 2.

Said composition comprises from about 10 to 60% of substances being able to form the skeleton of the lens-shaped pellets. Preferably a mixture of albumin and starch is used containing from about 20 to 40% albumin and from 2 to 5% starch (in total weight of the composition). After freezing and drying, these molecules form a highly porous and simultaneously mechanically stable skeleton that is dissolved rapidly in water.

Advantageously albumin belonging to such a composition is ovalbumin. Ovalbumin may appear in particular as an egg white preparation. Egg white is a sterile medium rich in protecting proteins within which it is possible to disperse the micro-organisms homogeneously. It may be however any other albumin (bovine albumin serum) or any protein having the same function.

Starch can be any type of starch and, in particular, natural as well as modified starches, dextrans, dextrins and maltodextrin. It can be substituted by any other hydrophilic macromolecule, particularly vegetal proteins or the hydrolysates thereof, collagens, gelatins, elastin hydrolysate or mixtures of above-mentioned substances.

Said composition also comprises from about 40 to 90% of a saturating substance. The saturating substance may be formed with one or more mixed salts or sugars. Such salts or sugars may be added as powder, brine or syrup. By using saccharose, preferably from about 60 to 80%, the composition has a lower water activity than 0.9. Consequently, the cellular damages occasioned by freezing and drying are limited and the development of micro-organisms is prevented in particular upon any transportation at room temperature.

According to one embodiment of the invention, the composition contains one or more types of micro-organisms. They can be strict anaerobic bacteria, aero-anaerobic or strict aerobic bacteria, psychrophilic bacteria, mesophilic or thermophilic bacteria, halophilic bacteria, enterobacteria, streptococci, staphylococci, pathogenic bacteria (Salmonella, Campylobacter, Yersinia, Listeria, *Pseudomonas aeruginosa*, Aeromonas, Vibrio, etc.), yeasts or moulds or fungi, bacteriophages or viruses, or protozoal cysts.

Advantageously, the present composition includes from $10^2$ to $10^{11}$, preferably from $10^2$ to $10^9$ micro-organisms per gram. Such a composition may be advantageously presented as pellets and in particular as lens-shaped pellets having a diameter in a range of 1 to 10 mm.

Such pellets have advantageously a mass from about 1 to 250 mg, preferably from about 2 to 100 mg, more preferably from 10 to 25 mg.

The pellets according to the present invention can be advantageously obtained with a manufacturing process comprising the following steps:

a) incorporating micro-organisms into the skeleton material, b) reducing water activity by adding progressively the saturating substance, c) shaping the pellets, and d) drying the pellets under vacuum and at a temperature lower than about −10° C.

Preferably the mixture is carried out as follows:

a) mixing albumin and micro-organisms, b) adding starch, and then c) adding saccharose.

Various drying modes are to be envisaged. Advantageously pellet drying is carried out in a desiccator in a period from about 12 hours to 10 days.

In view of an optimal stability, i.e. over a period of more than 12 months, the pellets may be stored at −70° C. in the presence of a dehydrating bag. They can however be preserved 3 months at −20° C. and 4 days at room temperature, making thus for example their transport easier since no particular and complexed transport condition is required.

A reconstitution medium convenient for a use in the present invention should limit at a maximum the osmotic shock upon the pellet dissolution. A 23 g/l synthetic sea salt solution is recommended as a reconstitution medium, since it presents a higher recovering level of the micro-organisms than the diluents usually used in microbiology such as Ringer, saline peptone or distilled water. Such a solution may be the one sold by Aquarium Systems (MENTOR, Ohio, USA) under the name Instant Ocean, or the DSM medium sold by SANOFI PASTEUR (Marnes la Coquette, France).

Pellet dissolution should be effected at room temperature. If the sample is not analyzed within half an hour after the reconstitution, it is to be recommended to maintain it in melting ice so as to guarantee a good stability.

Such pellets containing micro-organisms stable over time, homogeneous and able to be reconstituted as a suspension reproducibly, i.e. with amounts varying weakly from one test to another one, constitute actual reference materials particularly adapted for checking the reliability of measurements (internal and external quality control) in the bacteriology field for waters, drinks and foodstuffs generally, in pharmacy, cosmetics and environment.

This type of reference material may also be used advantageously for "challenge tests" in the foodstuffs field. For such a specific use, the pellets contain one or more micro-organisms. Pellets may be directly introduced into the product to be tested (alu-dish, salad bag, cooked dish, etc.). The products are then put in real preservation conditions and the progress of the contamination introduced quantitatively into the products is monitored according to the usual numbering procedures.

More generally, this new type of reference material may be used for the quantitative microbiological analysis:

checking the presence/absence of micro-organisms, checking the fertility of culture media, checking the efficiency of antibiotics, bactericide or bacteriostatic substances, checking sterilization (ultraviolet, chloration, ozonization, filtration, etc.).

According to another aspect of the invention, the pellets containing at least one type of micro-organisms may be advantageously used in specific products as starting agents for seeding the species so as to master a crucial microbiological parameter interfering in the fermentation process.

Thus, pellets containing yeasts, such as for example *S. cerevisae, S. calbergensis, S. ellipsoidus*, may be used to produce bread, high and low pressure beers, wine and other alcohols.

Pellets containing lactic bacteria may advantageously be used to produce fermented milks and yoghurt as well as in the pharmaceutical industry to produce products convenient for re-seeding intestinal flora.

Pellets containing activated fungal spores may be used directly or after dilution to a desired content of micro-organisms, in the foodstuffs field, particularly for cheese or salted food products. Said compositions may for example be spread or incorporated into the products to be converted, such as cheeze of salted food products.

Thus, pellets containing specific bacterial species, such as for example Rhizobium, Pseudomonas, Bacillus, Arthrobacter, Serratia and Azospirillum, may be used in agriculture and in the environment industry.

The present invention will be now illustrated without being limited by the following examples.

BRIEF DESCRIPTION OF THE FIGURES

Following figures illustrate moreover the present invention.

Figure 1:
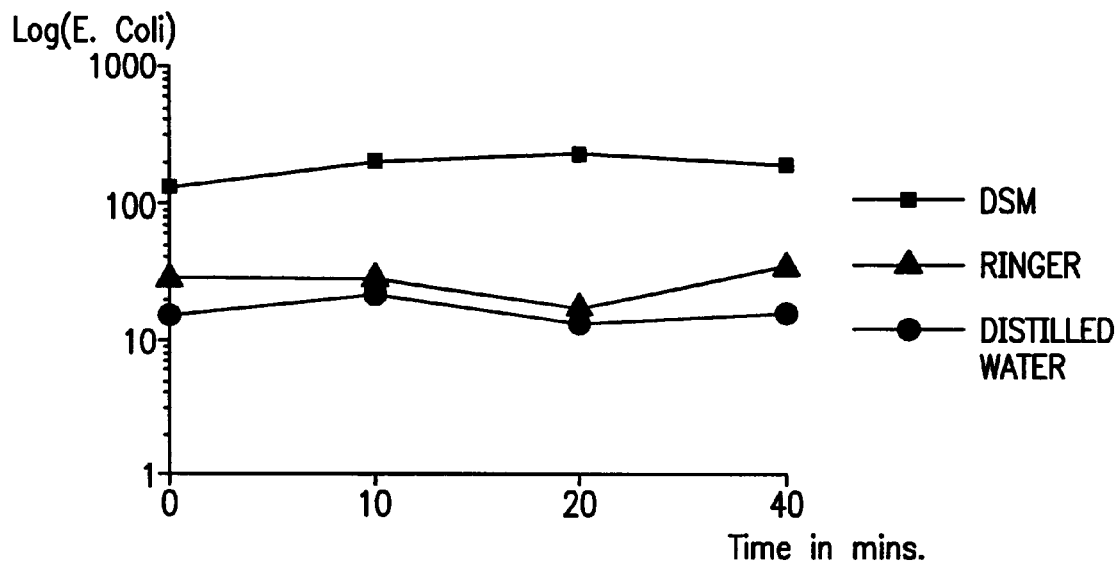
FIGS. 1 and 2 show the reconstitution of lens-shaped pellets containing respectively *Escherichia coli* and *Enterococcus faecalis* bacteria, in distilled water, RINGER medium and DSM medium.
Figure 2:
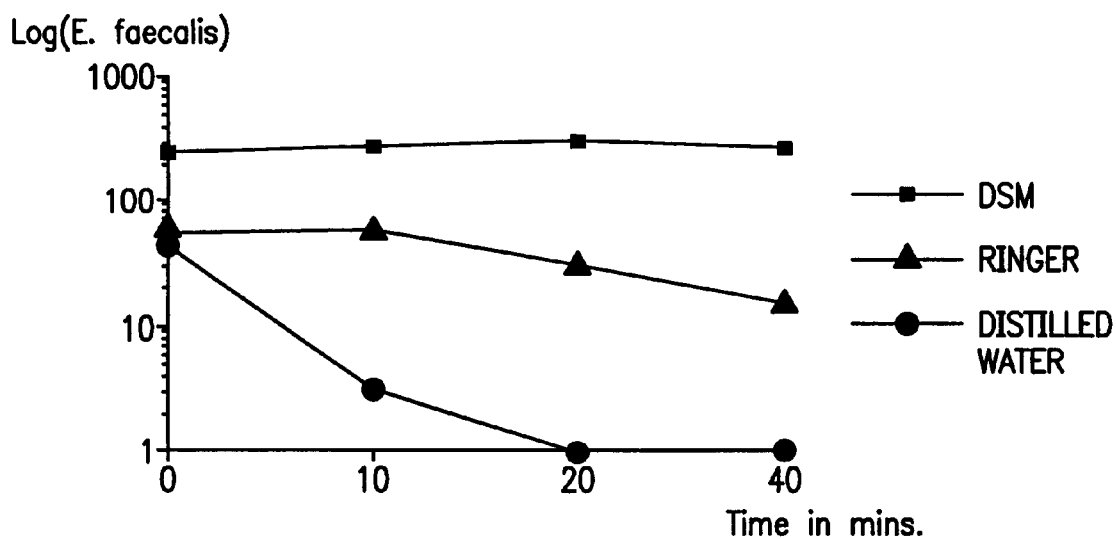

The ordinates show the values Log (*E. coli*) for FIG. 1 and Log(*E. faecalis*) for FIG. 2.

Figure 3:
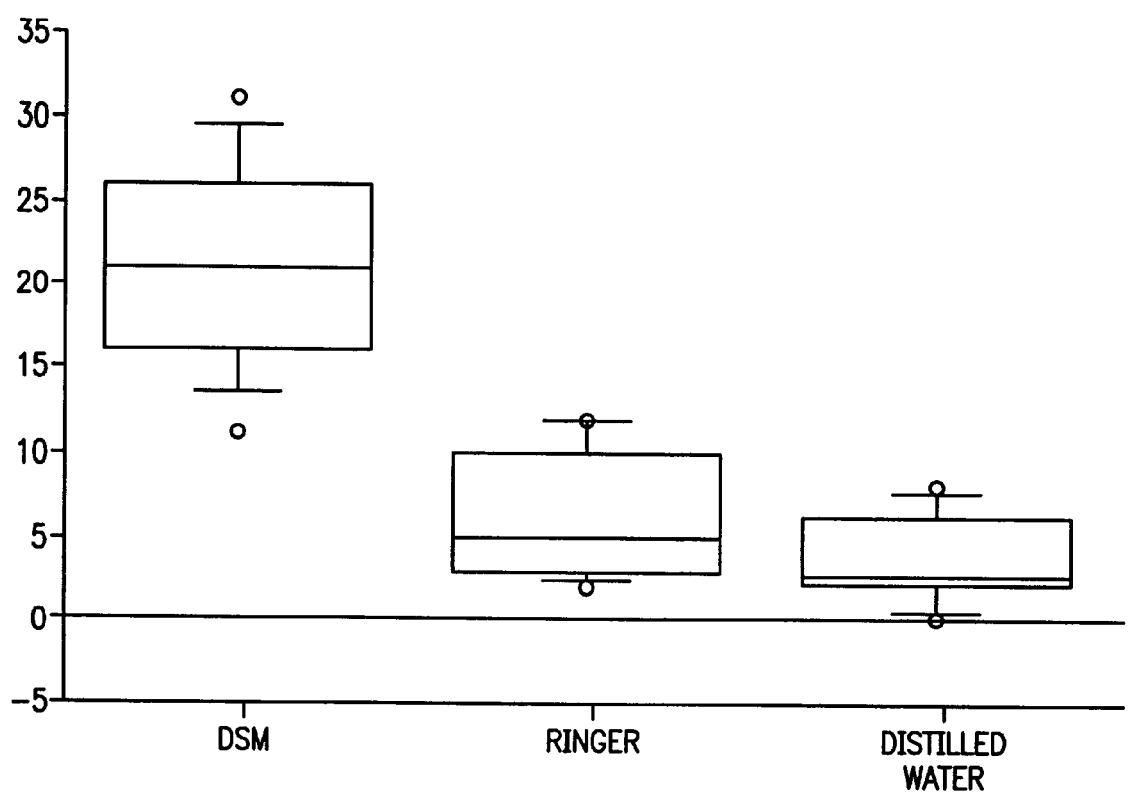

FIG. 3 is a statistical analysis of the reconstitution results obtained with *Escherichia coli* for each of the three reconstitution media. This figure shows the effect of the reconstitution medium with a study of the yield.

Figure 4A:
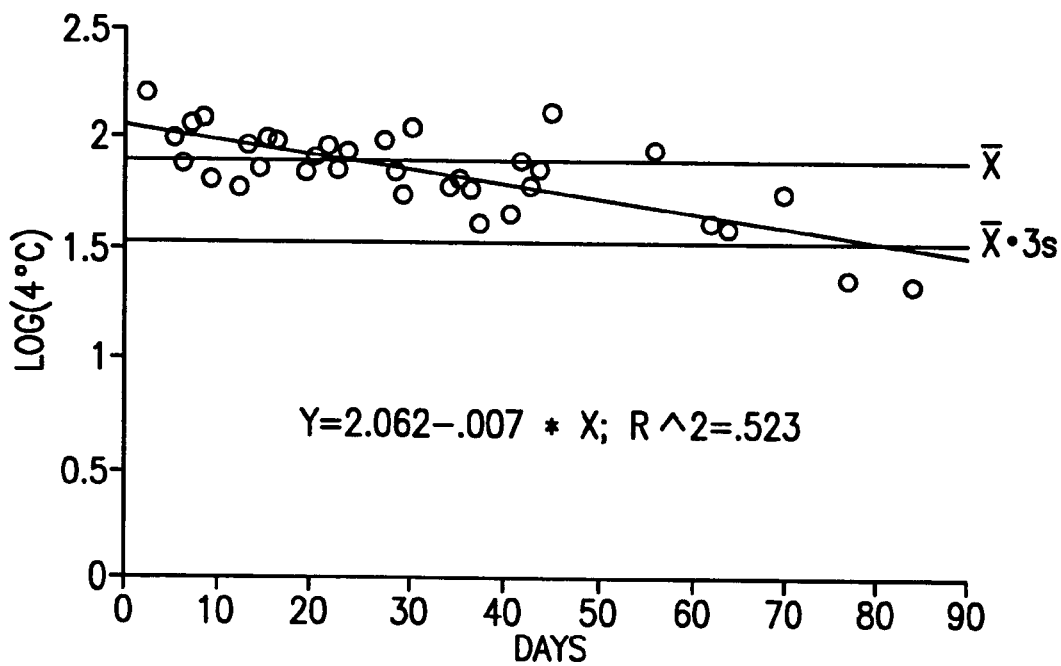
Figure 4B:
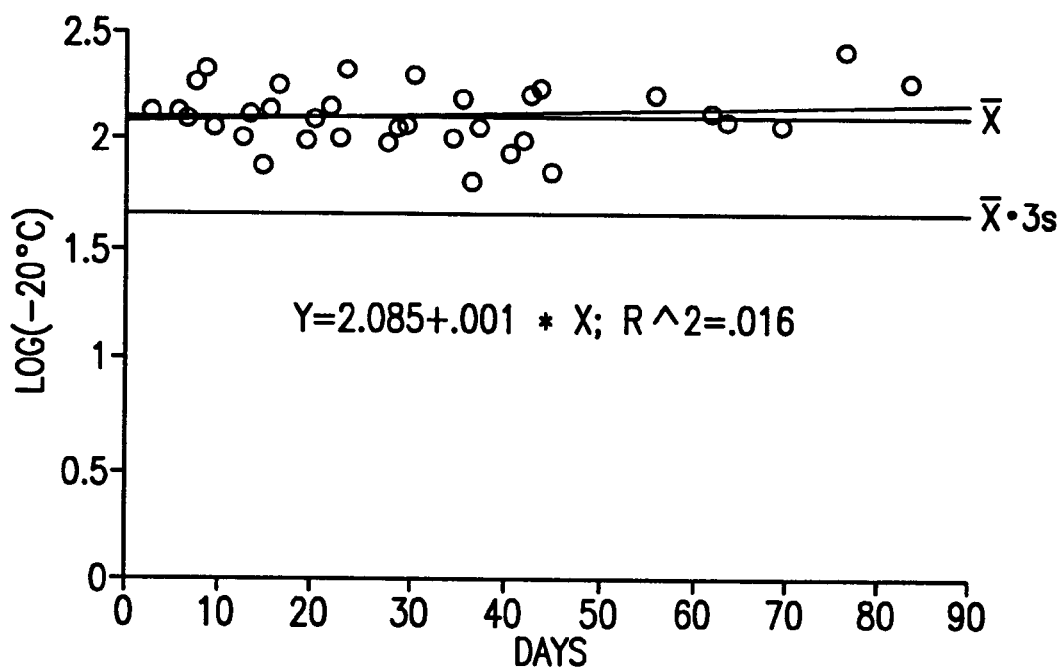
Figure 4C:
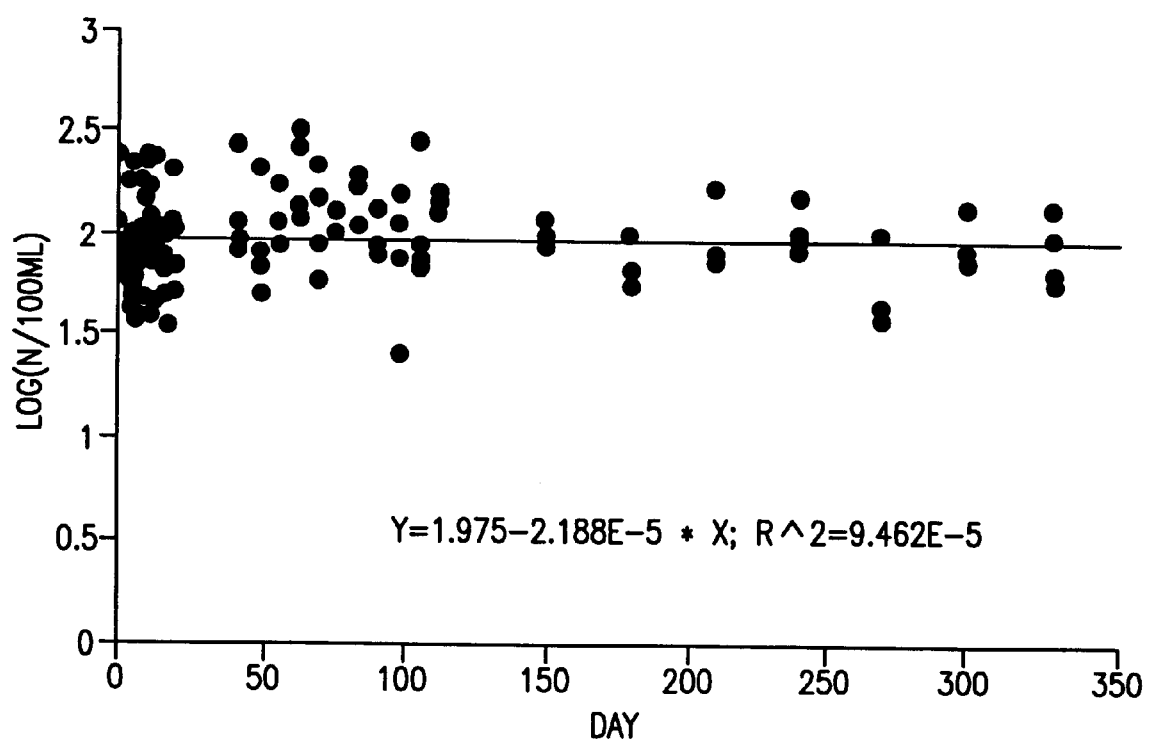

FIGS. 4A to 4C show the stability of lens-shaped pellets containing *Escherichia coli* and stored respectively at +4° C., −20° C. and −70° C. Thus, FIGS. 4A to 4C show the effect of the storage temperature with a study of the stability of the reference materials, with in FIG. 4A *E. coli* species preserved at +4° C., in FIG. 4B *E. coli* preserved at −20° C. and in FIG. 4C *E. coli* preserved at −70° C.

Figure 5A:
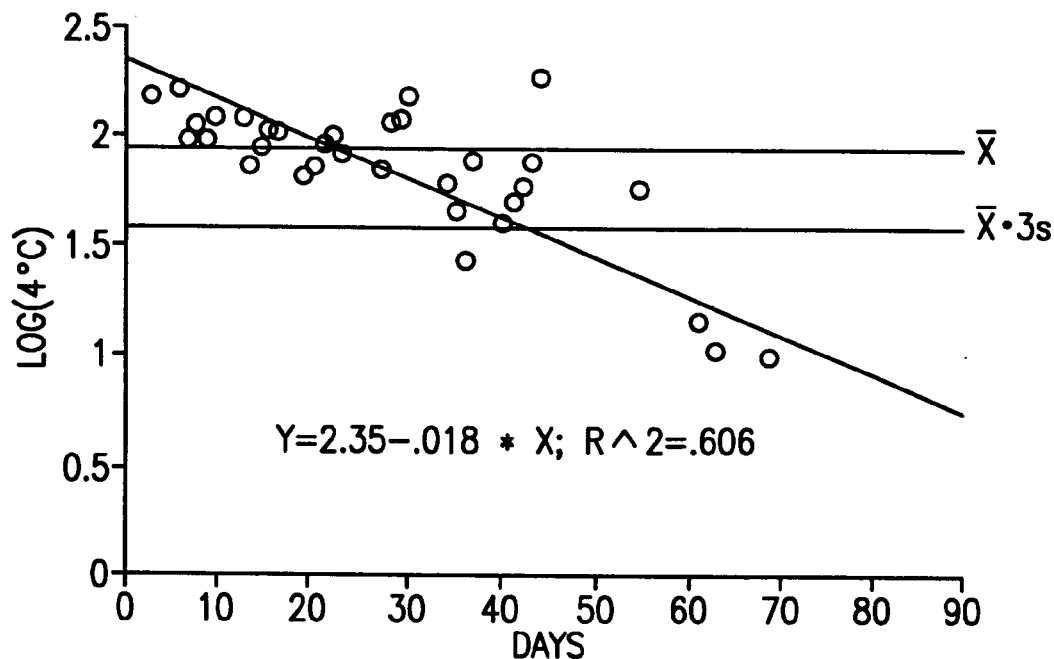
Figure 5B:
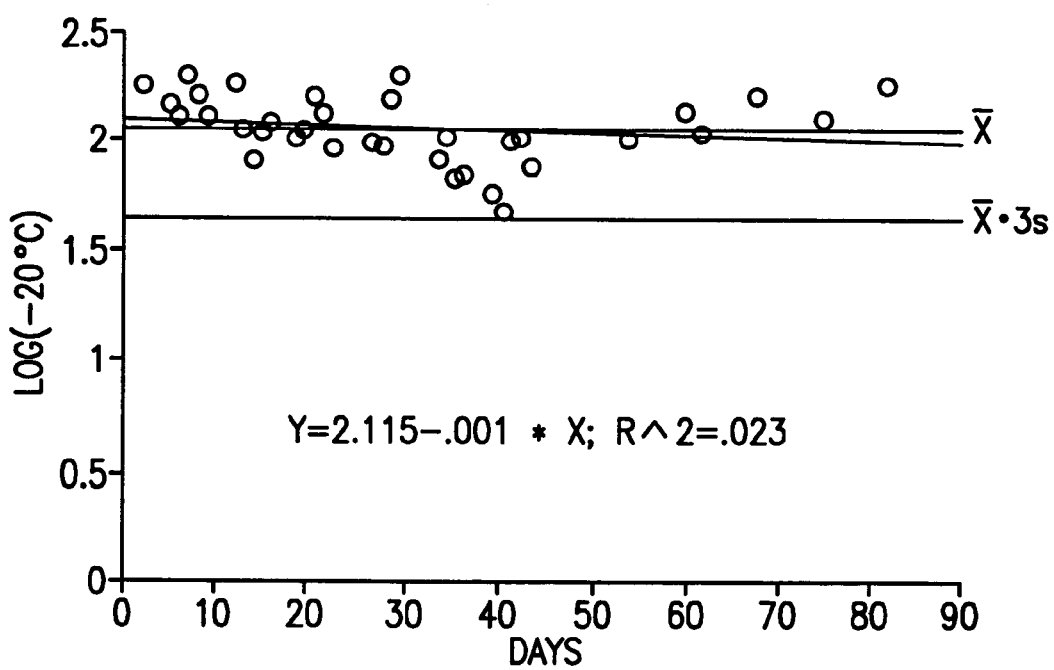

FIGS. 5A and 5B show the stability of lens-shaped pellets containing *Klebsiella plantlicola* and stored respectively at +4° C. and −20° C. Thus, FIGS. 5A and 5B show the effect of the storage temperature with a study of the stability of the reference materials, with in FIG. 5A *Klebsiella plantlicola* species preserved at +4° C. and in FIG. 5B *Klebsiella plantlicola* preserved at −20° C.

Figure 6A:
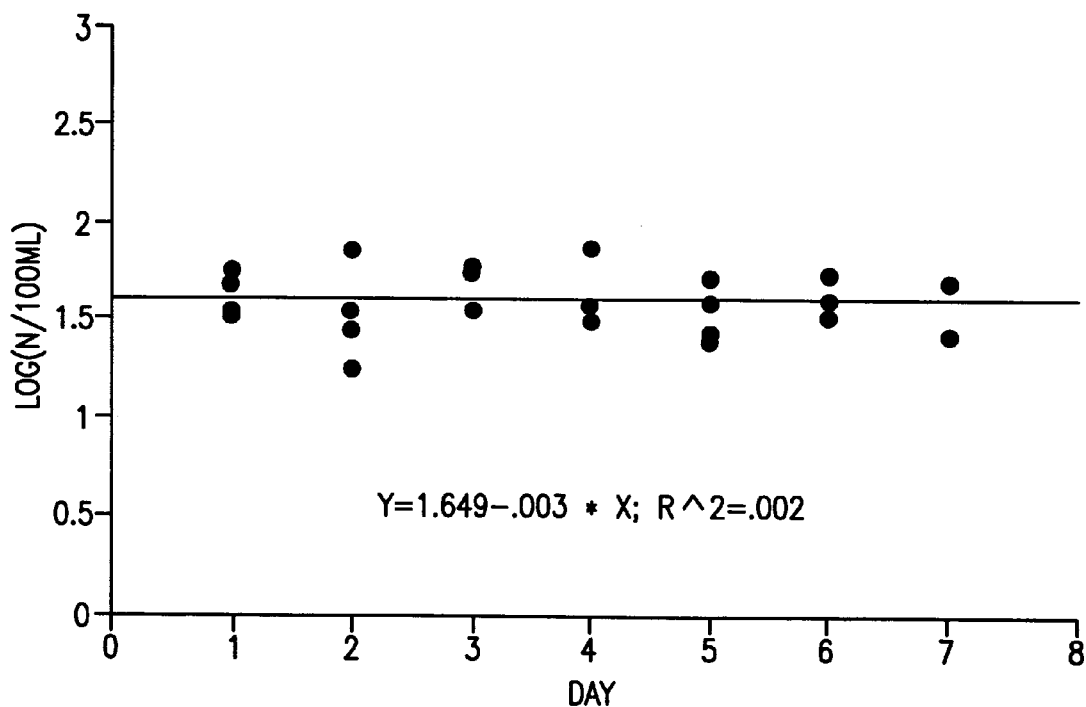
Figure 6B:
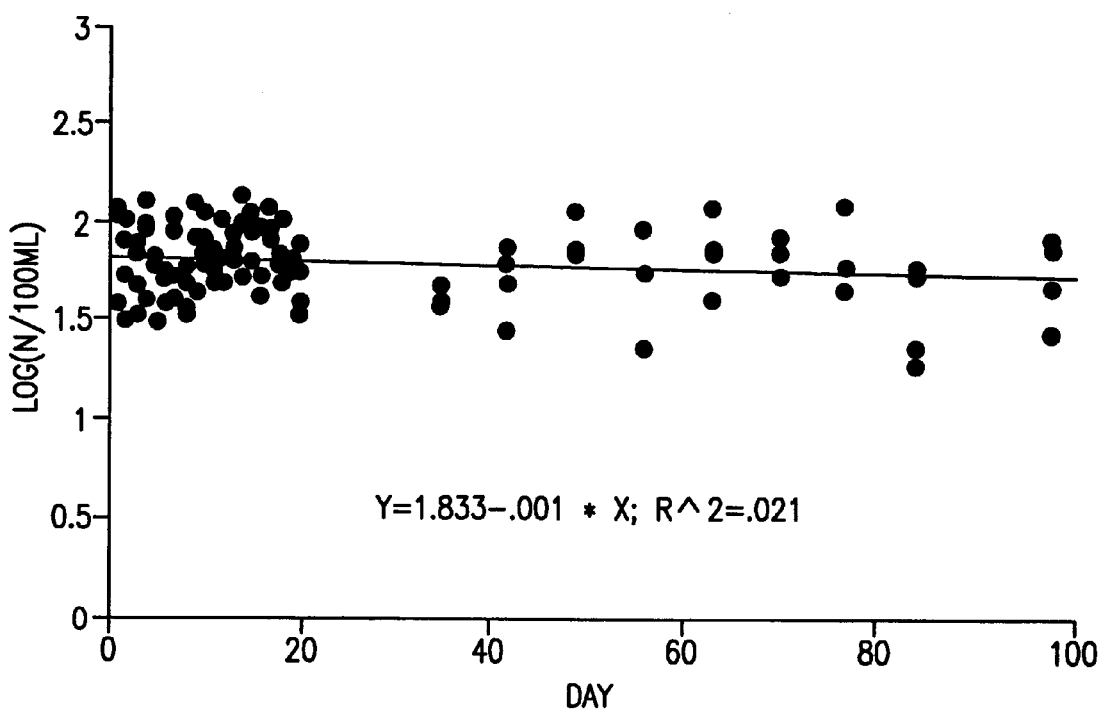
Figure 6C:
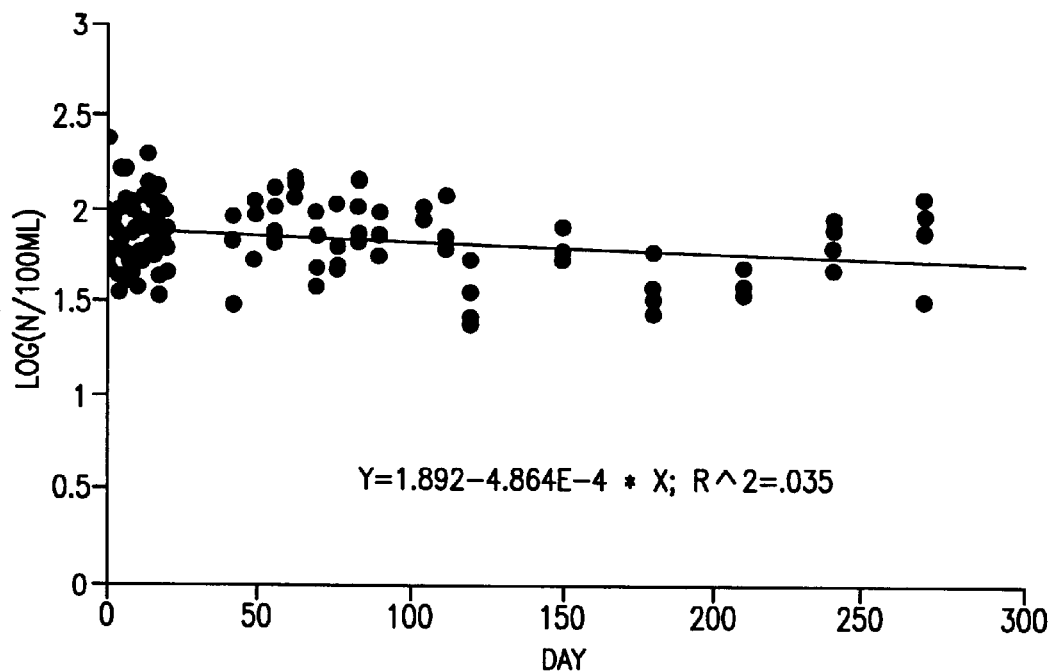

FIGS. 6A to 6C shows the stability of lens-shaped pellets containing *Staphylococcus aureus* stored respectively at +4° C., −20° C. and −70° C. Thus, FIGS. 6A to 6C show the effect of the storage temperature with a study of the stability of reference materials, these figures corresponding to *Staphylococcus aureus* preserved at +4° C., −20° C. and −70° C.

Figure 7A:
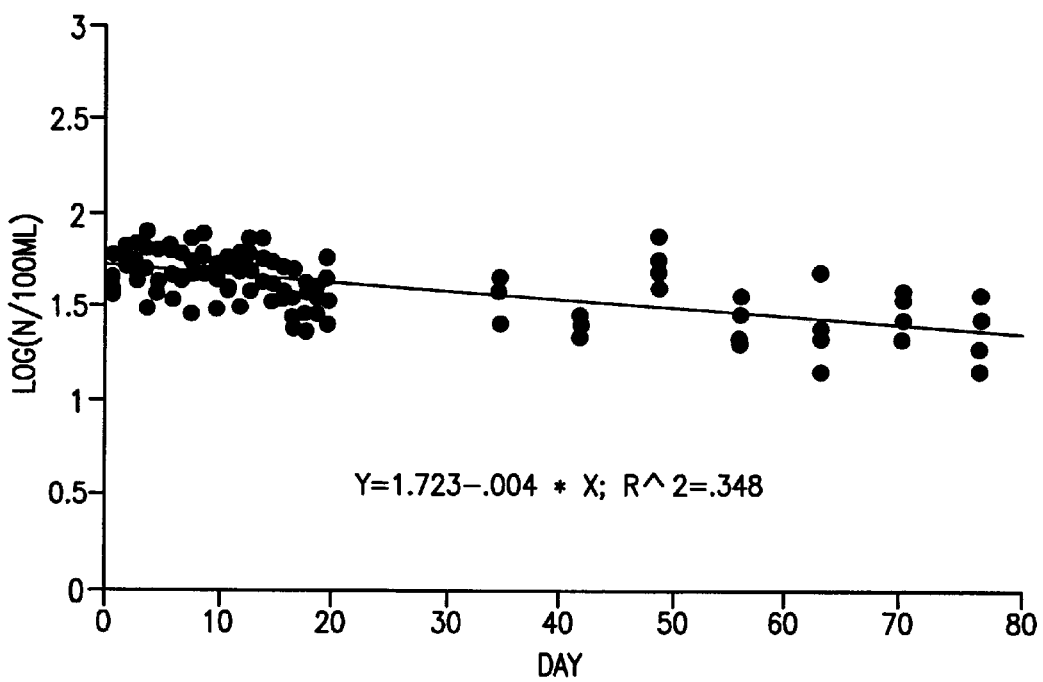
Figure 7B:
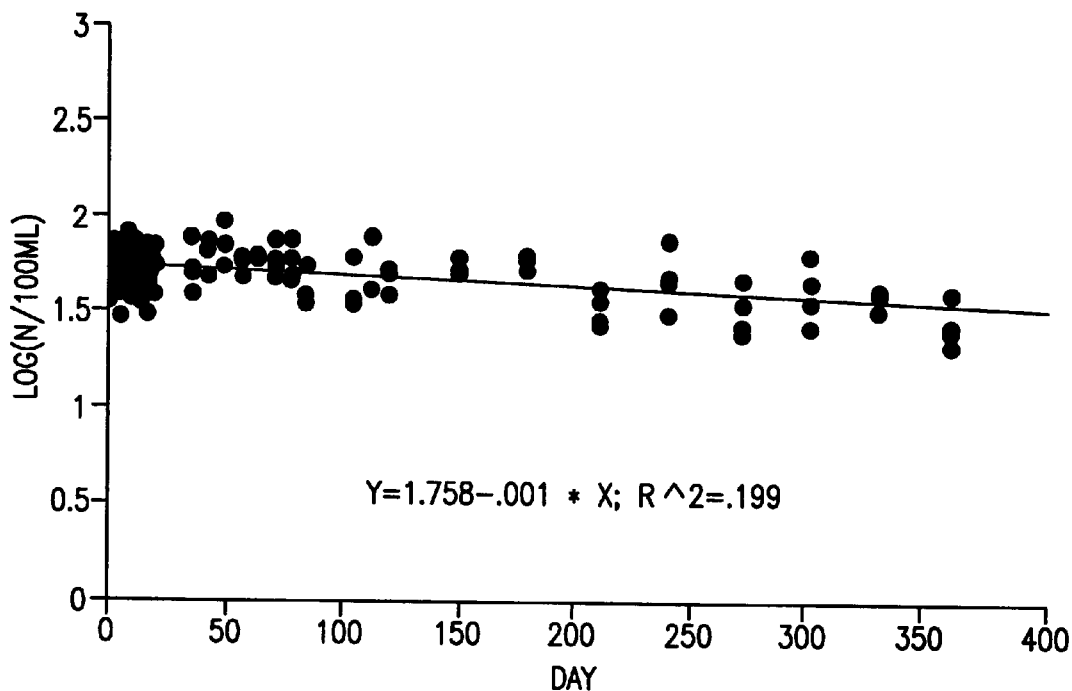
Figure 7C:
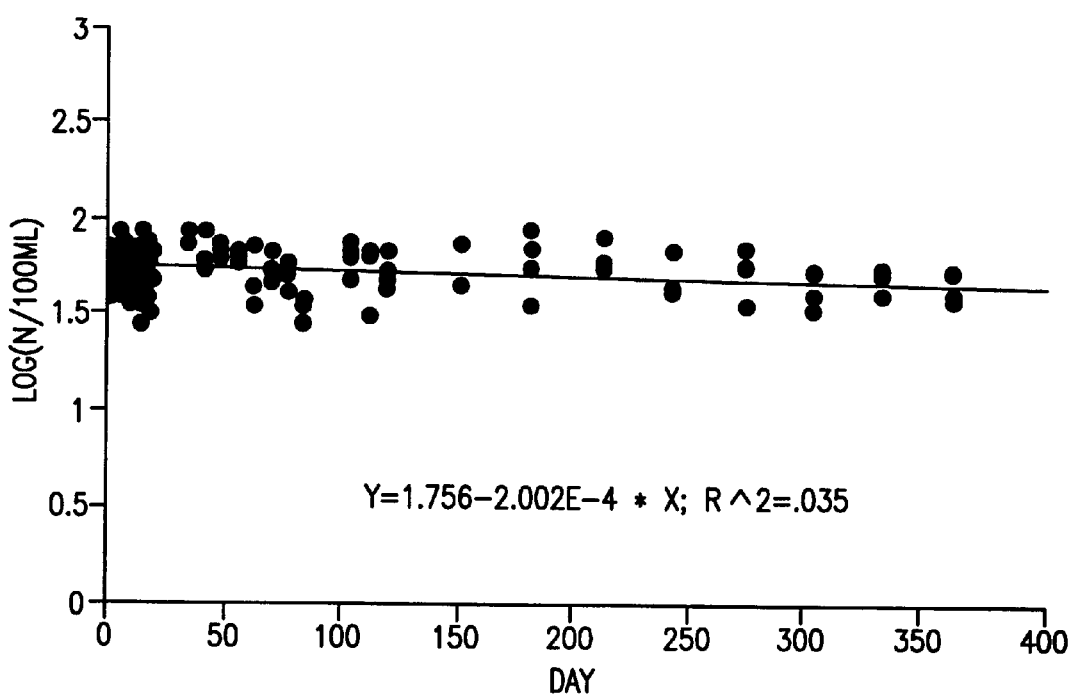

FIGS. 7A to 7C show the stability of lens-shaped pellets containing *Enterococcus faecalis* species stored respectively at +4° C., −20° C. and −70° C.

Figure 8A:
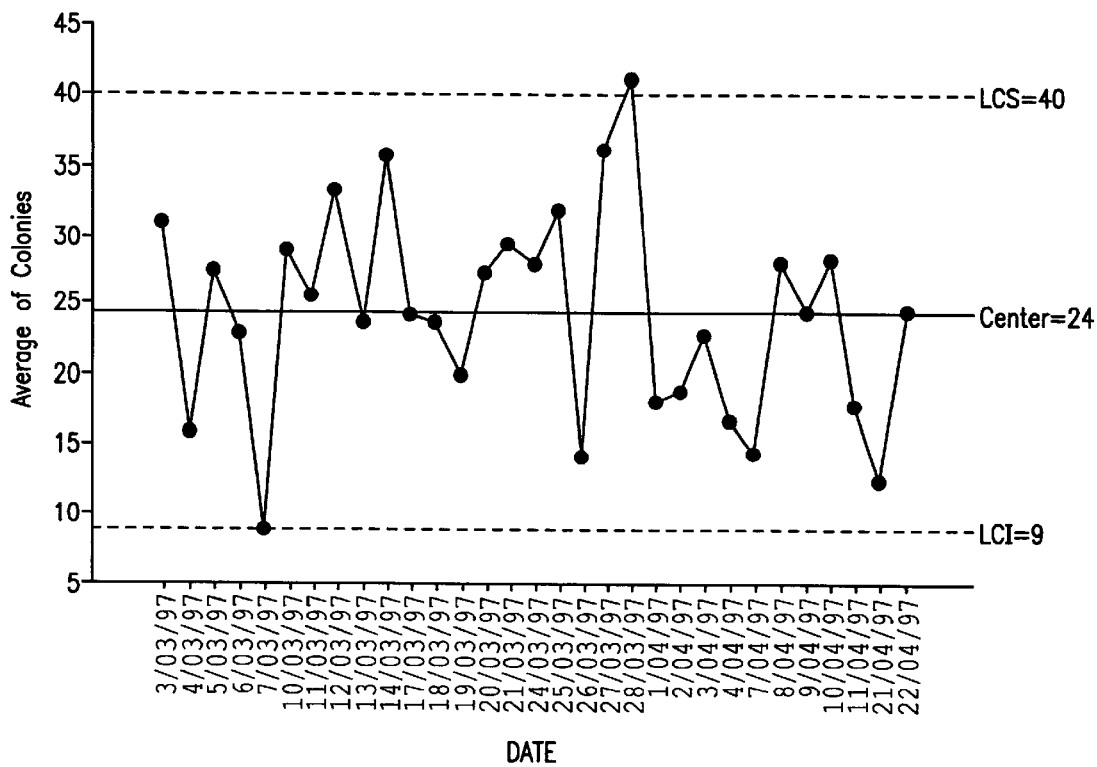
Figure 8B:
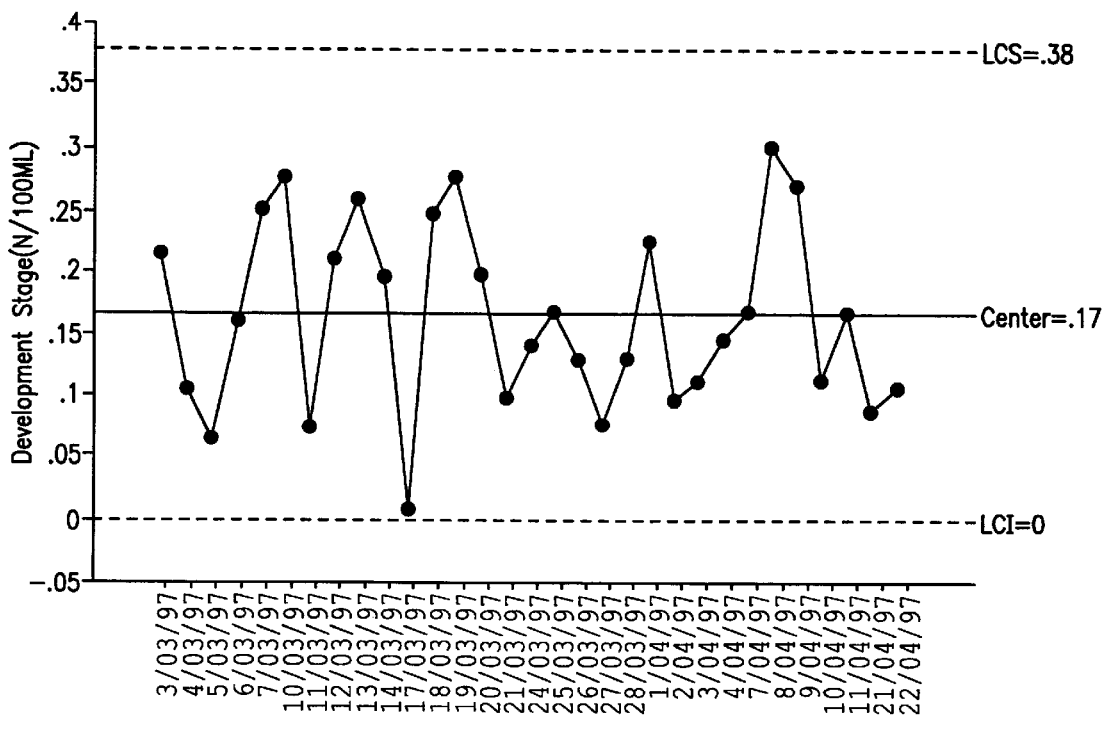

FIGS. 8A and 8B show the checking maps respectively for the average and the standard deviation obtained for the numbering of *Enterococcus faecalis* species over a period of more than 30 days.

Figure 9A:
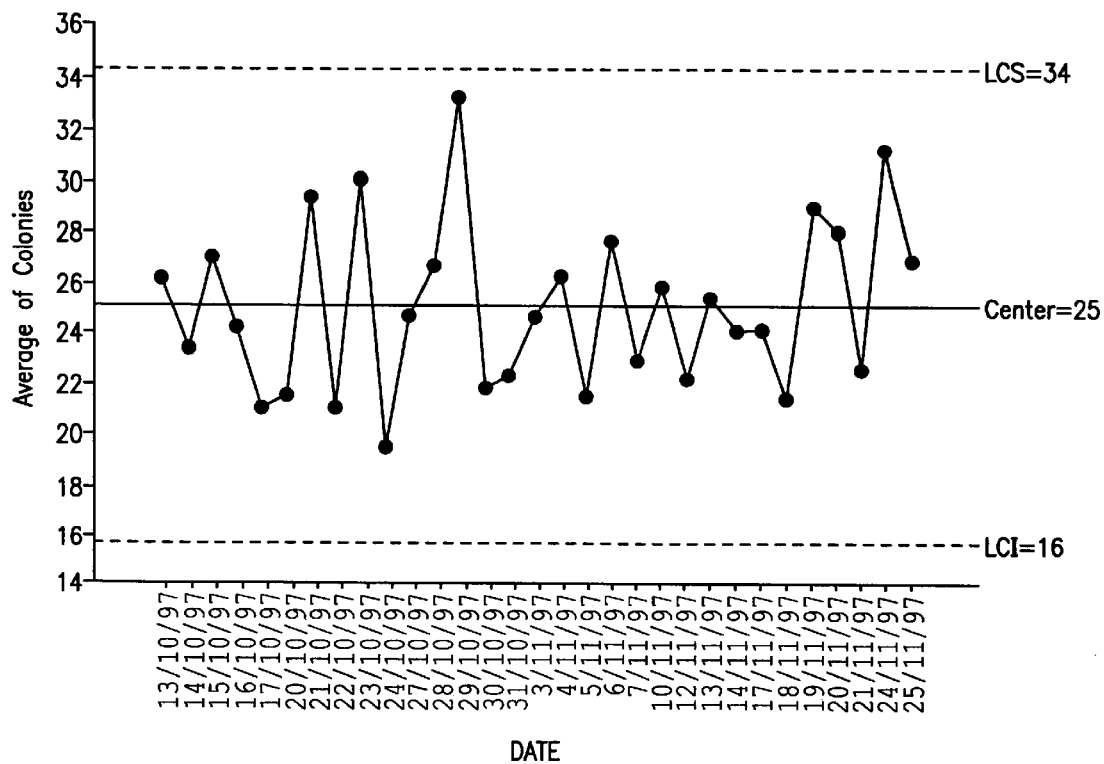
Figure 9B:
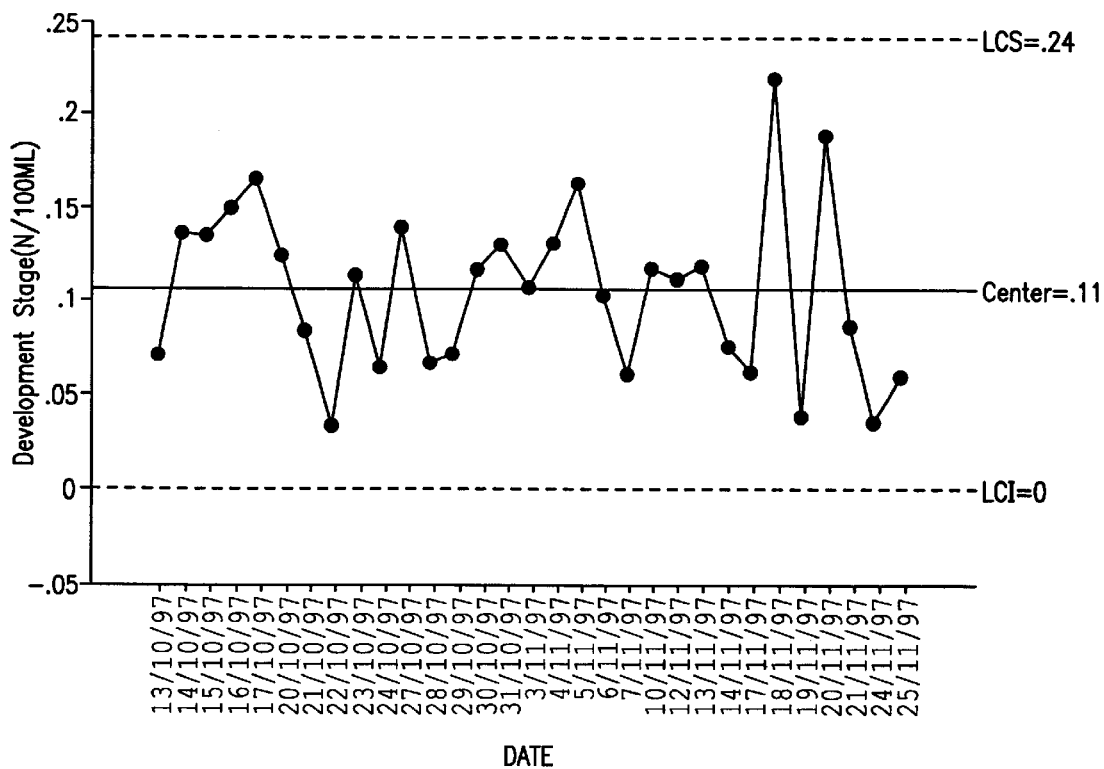

FIGS. 9A and 9B show the checking maps, respectively, for the average and the standard deviation obtained for the numbering of *Enterococcus faecalis* over a period of more than 30 days.

Figure 10A:
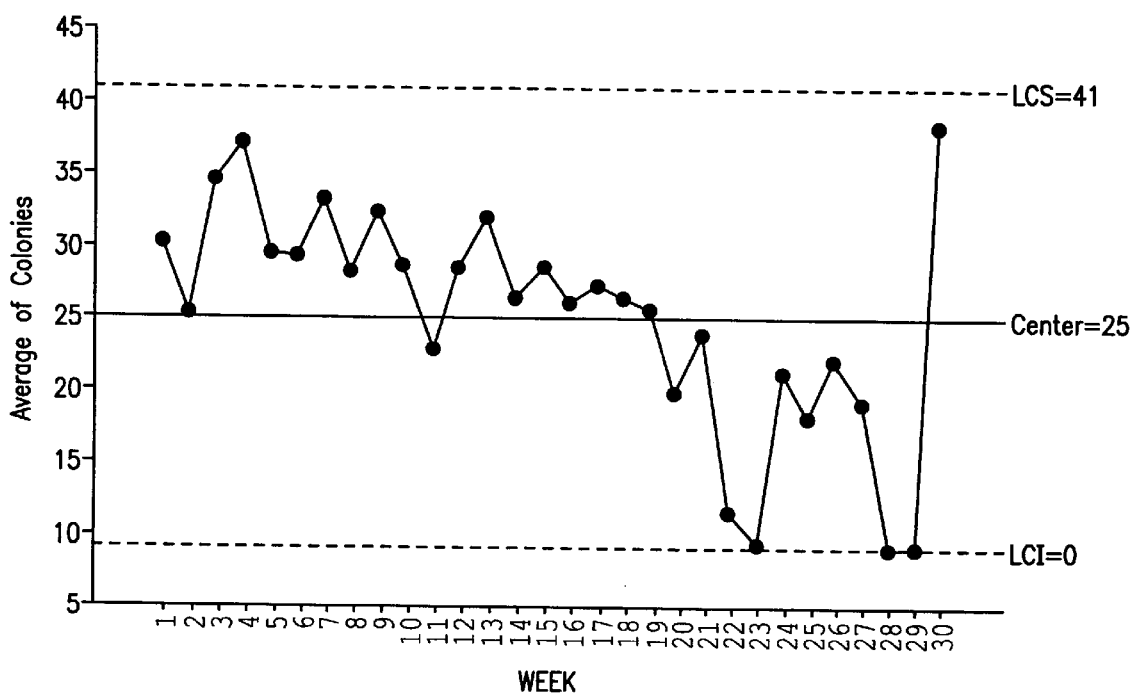
Figure 10B:
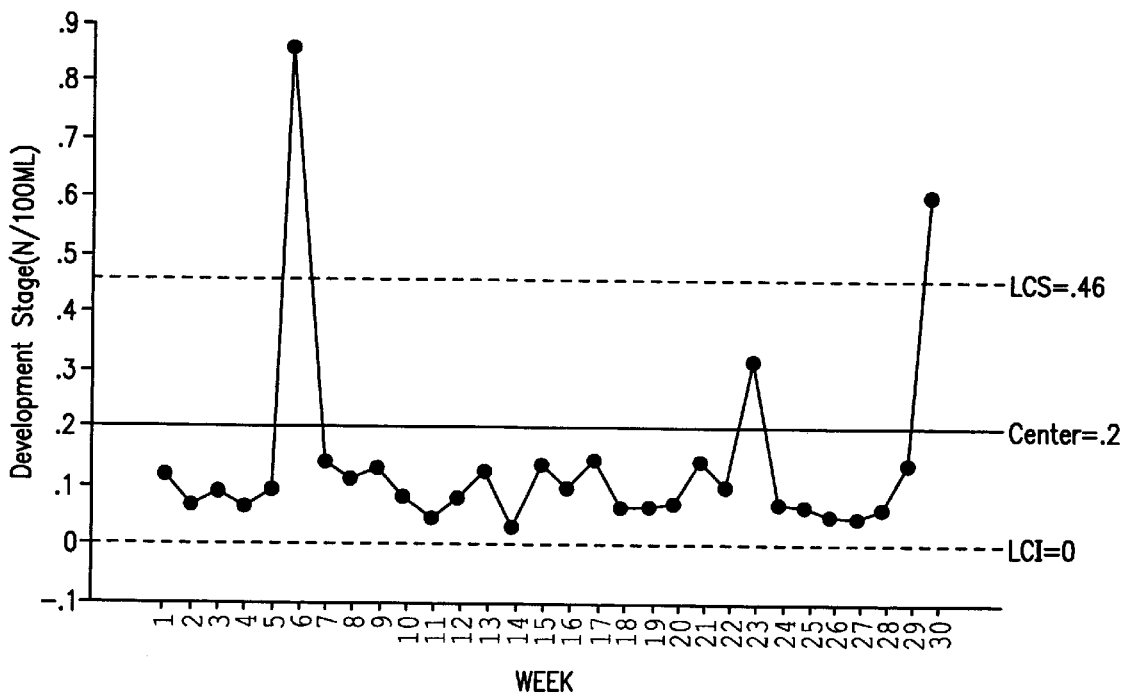

FIGS. 10A and 10B show the checking maps respectively for the average and the standard deviation obtained for *S. aureus* over a period of 30 weeks.

Figure 11A:
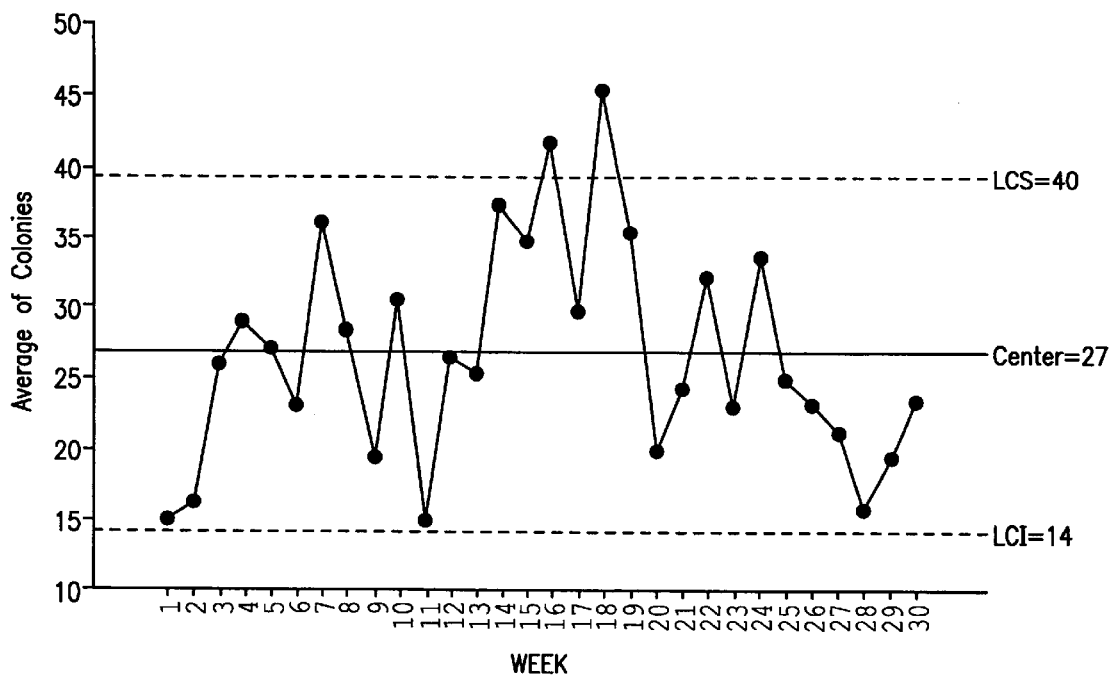
Figure 11B:
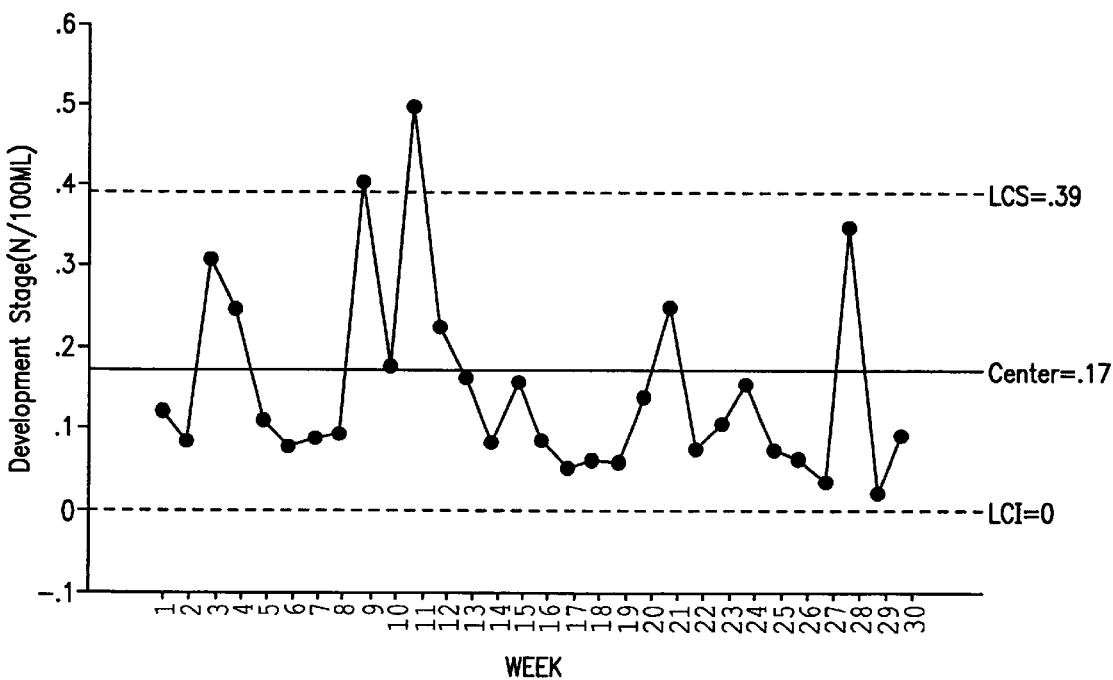

FIGS. 11A and 11B show checking maps respectively for the average and the standard deviation obtained for *Clostridium sporogenes* species over a period of 30 weeks.

EXAMPLE 1

Manufacture of Lens-shaped Pellets

1. Manufacture of the Pellets

Bacteria either as culture broths or colonies re-suspended into 0.25 ml DSM medium are mixed during 3 min. into 10 ml egg white (about 15 g).

1.2 g starch are then added and the whole is mixed during 30 sec.

32 g of icing sugar are progressively added while maintaining mixing during 7 min.

Finally mixing is continued during 3 min. with no addition.

Mixing is carried out for such different steps in a mixer adjusted to 700 revolutions per minute.

The resulting composition is then distributed into droplets on a plastic plate by means of a 10 ml syringe with a needle of 1.2×40 mm.

The plate is put in a desiccator and then the whole is placed under vacuum and submitted to −20° C. during 4 days.

The so-obtained lens-shaped pellets or lenticles are recovered and then stored at +4° C. or −20° C. in a flask provided with a desiccating bag.

2. Bacterial Sample

The bacterial sample may be added to the mixture under two different forms:

as a broth, as colonies recovered from a Petri dish.

The sample as a broth is used when the post-drying mortality has been judged as important upon a first conditioning trial as lenticles. In fact, the broth allows after centrifugation for a high concentration of bacteria that is difficult to obtain with colonies.

The sample as colonies has this advantage to be easily quantifiable. It is used when the post-drying survival rate is judged as correct. Its use implies the addition of 0.25 ml DSM, thus preventing the modification of the amounts with respect to the mixture using the broth.

3. Drying of the Pellet Batch

A drying test at different temperatures of a same batch of lenticles of *E. coli* has been carried out.

Procedure:
  10 droplets of a same manufacture batch are placed for drying at +44° C.
  10 other droplets are placed for drying under a laminar flow hood at ordinary temperature.
  The last 10 droplets are placed at −20° C. inside a desiccator in which a vacuum has been established.
  After 2 days drying, the lenticles are reconstituted in a 9 ml tube of RINGER medium.
  5 ml of each of the tubes are then filtrated on Tergitol TTC medium (AFNOR T 90-414).

Results

The results are represented in Table 1 below.

These results show that the mixture at −20° C. inside a desiccator under vacuum allows to obtain a higher viability with respect to other drying processes.

EXAMPLE 2

Reconstitution of Bacterial Solutions From Lens-shaped Pellets

1. Stability of the Reconstituted Sample at Room Temperature a) *E. coli* ($WR_1$ Species Available From the Dutch Collection RIVM).

Procedure:
  4 lenticles of *E. coli* obtained according to example 1 are placed respectively into tubes containing the reconstituting media DSM, RINGER and Sterile Distilled Water,
  2 ml of each tube are then poured at various time intervals (0, 10, 20, 40 minutes) in a flask (Pasteur microbio type) containing 400 ml of tap water,
  The results are summurized in FIG. 1.
  2 filtration replicates are carried out on each flask (automatic filtration of 100 ml on an automation system SARAH).

It is to be observed for *E. coli*:
  a stability in each of the reconstituents,
  a well higher number of colonies (about 10 times more) for the reconstituted lenticle in DSM compared to both other lenticles reconstituted respectively in RINGER and sterile distilled water media.

a) *Enterococcus faecalis* (species available at the Czech Collection under n° 2541)

Procedure:
  An *Enterococcus faecalis* lenticle obtained according to example 1 is put in a tube of each reconstituent (DSM, RINGER, Sterile Distilled Water);
  1 ml of each tube is then poured at different time intervals into a flask (Pasteur microbio type) containing 400 ml of tap water.
  2 replicates of filtration are carried out on each flask (automatic filtration on an automation system SARAH).
  FIG. 2 show the so-obtained results.

It is to be observed for *Enterococcus faecalis*:
  in sterile distilled water, a quick loss of the number of colonies recovered depending on the contact time of the lenticle with the reconstituent (from 55 to 0 colony recovered within 20 minutes),
  in RINGER, a slow loss of the number of colonies recovered depending on the contact time of the lenticle with the reconstituent (from 47 to 15 colonies within 40 minutes).

In DSM, a stability of the number of colonies depending on the time with a well higher recovering level.

1. Yield of the Different Reconstituents

These tests serve to show that the DSM medium allows for a better recovery of colonies compared to other diluents like RINGER or sterile distilled water.

Procedure:
  10 *E. coli* tablets obtained according to example 1 are reconstituted in each of the three reconstituents (DSM, RINGER and sterile distilled water).
  All the tubes are put at +4° C. (water+Ice Pack®) to prevent any temperature effect.
  Each tube content is wholly poured into a flask of 400 ml of tap water (Pasteur microbio type flask).
  All the flasks are then filtered by automatic filtration of 100 ml on the automation system SARAH.

Results:

These results are summarized in FIG. 3

It is to be observed that:
  for DSM, on average about 22 colonies are recovered per filtration,
  for RINGER, on average about 7 colonies are recovered per filtration,
  for sterile distilled water, on average about 3 colonies are recovered per filtration.

Thus, for the same *E. coli* lenticle batch, about 3 more times colonies are recovered when DSM is used as a reconstituent compared to RINGER and about 7 more times colonies compared to sterile distilled water.

Thus, these results (2.1 and 2.2) show that DSM provides a better stability and a better yield upon the reconstitution of the lenticles.

Each of the manipulations effected through the lenticles should be preferably carried out in cold condition (for a guaranteed stability beyond 40 minutes) and in DSM medium.

EXAMPLE 3

Validation of the Lenticle Batches

Five species of *Escherichia coli, Klebsiella planticola* (species available at ATCC under n° 33 531), *Enterococcus faecalis, Staphylococcus aureus* and *Clostridium sporogenes* have been conditioned into lenticles, as described in example 1.

Procedure:
  The validation is carried out by numbering 30 lenticles after drying.
  Each of the lenticles is put into a tube containing 9 ml of DSM.
  The tubes previously at room temperature are placed at +4° C. (water bath+Ice Pack®) as soon as the lenticle has dissolved in DSM (dissolution with Vortex®).
  A dissolution is carried out when the lenticle concentration is too high.
  Then 5 ml of each of the dilutions are filtered.

Results:

The results are shown in table 2 hereafter. These results show that for all the seeds being studied the reproducibility coefficient (SR) is lower than 0.20 in logarithmic units. SR measures the variability of the results obtained when measures are made on different pellets within a same laboratory.

EXAMPLE 4

Stability of Stored Batches

Procedure:

Lenticles are preserved at +4° C., −20° C. or −70° C. in flasks provided with a desiccating bag (a same batch is divided into two identical quantities stored at two different temperatures).

Each day, two lenticles are tested, for each batch and for each of the preservation temperatures (+4° C., −20° C. and −70° C.).

Each lenticle is put in a tube containing 10 ml DSM and then dissolved lo in a Vortex® at room temperature. The so-reconstituted samples are put at +4° C. before filtration.

Filtration is carried out in two replicates of 5 ml for each lenticle.

Thus there is each day the sum of four numberings for each of both preservation temperatures (+4° C., −20° C. and −70° C.).

The monitoring of this value allows to establish the regression line enabling the progression of the batch to be visualized.

Results:

The stability results are represented as regression lines for:

*E. coli* (FIGS. 4A, 4B and 4C),
*K. planticola* (FIGS. 5A, 5B),
*S. aureus* (FIGS. 6A, 6B and 6C),
*E. faecalis* (FIGS. 7A, 7B, 7C).

The null slopes obtained by linear regression show that for the four seeds being studied the batches are stable during:

1 week at +4° C.,
3 months at −20° C., and
1 year at −70° C.

These stabilities are wholly compatible with an industrial use.

EXAMPLE 5

Use of the Lens-shaped Pellets as Reference Material

The reference materials may be used for checking the fertility in culture media, the statistical management of processes and the capacity tests by comparison between laboratories.

1. Checking Fertility in Culture Media

The standards AFNOR T90-432 and T90-433 impose quality criteria for manufacturing the culture medium in microplate.

Quality control must be effected on each batch of manufactured microplates. The microplates to be tested are taken in either a randomized or systematic manner so as to make a sample according to the standard AFNOR 06-023, respecting the normal taking level (9 microplates checked for a batch size of 1000 microplates manufactured).

The fertility of the culture medium is measured with the ratio between the number of micro-organisms being observed with the batch of tested microplates and the number of micro-organisms being expected with a stable reference material (target value). The concentration level to be implemented after reconstitution of the reference material should be around the maximum precision of the method, namely 500 bacteria/100 ml. The acceptation thresholds for the microplate batch in the test are 0.66 to 1.55 times the target value (66%<yield (%)<150%).

The strain to be tested for the standard T90-433 is *E. coli* WR1.

The strains to be tested for the standard T90-432 are *E. faecium* WR63, *E. faecalis* CCM 2541 and *E. hirae* 2423.

Tables 3 to 6 report for each of the strains the results of fertility obtained on the production of microplates in 1997. They show a perfect management of the production by the manufacturer. In fact, 90% of the produced batches meet the fertility criterium mentioned in the standards.

2. Statistical Management of the Processes (Internal Quality Control)

Before implementing the internal quality control, the laboratory should calibrate their analytical chain. For this purpose, in order to take the results obtained in the previous examples into account, the following protocols have been established:

Reconstitution Protocol for the Reference Material:

Take the tube(s) out of the freezer, with sterile tongs, take the pellet(s) necessary for checking (lens-shaped pellets produced as described in example 1), place again the tube(s) immediately in the freezer, let stay the pellet(s) 25 minutes at room temperature, dip each pellet into a tube containing 18 ml of a diluent special for pellets (mother suspension), let stay 15 minutes at room temperature without stirring, stir gently the tube(s) during 30 seconds, if the seedings are not carried out within the hour following the reconstitution, preserve the tube(s) of mother suspension in melting ice (securing a four-hour stability).

Protocol of Preparation for Diluent Special for Pellets:

Dissolve 22.5 g of sea salts (Instant Ocean) into 1 liter of distilled water, verify salinity (20+/−3 for 1000) or conductivity (25000+/−4000 uS.cm$^{-1}$), adjust pH (7.9+/−0.5), distribute into tubes of 18 ml, autoclave treating at 120° C. during 15 minutes.

Calibration protocol:

Use the mother suspension:
  pellets 1 and 2: filter 0.5 ml,
  pellets 3 and 4: filter 1.0 ml,
  pellets 5 and 6: filter 2.0 ml,
  pellets 7 and 8: filter 4.0 ml,
  pellets 9 and 10: filter 8.0 ml.

Verify the linearity of the results by linear regression.
  From the regression line equation, determine the filtration volume to be proposed for each material so as to obtain 25 colonies on the membrane.

Once centered on such target value of 25 colonies, the laboratory should arrange their internal control so as to find deviations, out-of-center drifts, repeatability of reproducibility problems. Depending on the analytic activity of the laboratory, this internal control provides A Daily Coverage:

The big laboratories making a hundred of analysis each day may test 4 pellets each day. FIGS. 8A and 8B, and 9A and 9B represent the checking maps for the average and the standard deviation routinely obtained from the pellets according to the invention containing *E. coli* and *E. faecalis* over a period of 30 days A weekly coverage:

The small laboratories making a hundred of analyses each week may test 5 pellets each week, namely one pellet per day. FIGS. 10A and 10B, and 11A and 11B represent the checking maps for the average and the standard deviation routinely obtained with pellets according to the invention containing *S. aureus* and *C. sporogenes* over a period of 30 weeks.

Through this type of internal control, the microbiology laboratories have now at their disposal an alarm system in real time (daily coverage) or in deferred time (weekly coverage) with a possibility of selecting the error causes and implementing the corrective actions.

3. Capacity Tests of Laboratories by Inter-comparison (External Quality Control)

A capacity test consists in using inter-comparisons to determine the performance of a laboratory in terms of trials or measurements. The participation to capacity test systems give the laboratories an objective possibility to estimate and demonstrate the reliability of the data they produce. The laboratories complete thus the internal procedures of quality management by providing an extra external measurement of their expertise in terms of tests.

The Association Générale des Laboratoires d'Analyse de l'Environnement (A.G.L.A.E.) has organized in April 98 an inter-laboratory test grouping 55 French laboratories (continental France and Overseas Departments). Pellets manufactured as described in example 1 have been used as reference material.

Results obtained upon a numbering of the enterococci on a pellet batch containing *Enterococcus faecalis* species are summarized in table 7.

In table 7 hereafter, $S_u$ measures the variability of results obtained when measurements are carried out on the same pellet within a same laboratory.

r corresponds to the variability of the results obtained when measurements are carried out on different pellets within a same laboratory.

R measures the variability of the results obtained when measurements are carried out on different pellets and by different laboratories.

The value of 0.10 obtained for $S_u$ shows that pellets dissolve homogeneously.

The value of 0.18 obtained for r shows the good homogeneity of the pellet batch.

The value of 0.3 obtained for R is a value comparable with the results usually obtained in this type of inter-laboratory test and thus validates this technique (stability of the pellets upon the transfer and the easy implementation in the laboratories).

The interest of the present invention in the frame of these inter-laboratory tests lies on the possibility to preserve the pellets even at room temperature.

Thus, the inter-laboratory tests carried out the past years required to provide each laboratory with a sample consisting in an artificially contaminated liter of water. Such sample should thus reach each laboratory within a few hours so as to be sure that all the laboratories worked in the same conditions.

Pellets according to the present invention allow to solve this problem and make the organization of such test easier.

TABLE 1

| Drying | Average number of colonies on 10 dishes |
|---|---|
| +44° C. | 24 |
| under a laminar flow hood | >100 |
| −20° C. | >100* |

*Dishes twice loaded than at room temperature

TABLE 2

| | E. coli | K. planticola | E. faecalis | S. aureus | C. sporogenes |
|---|---|---|---|---|---|
| Mini = | 8 | 6 | 8 | 28 | 8 |
| Average = | 24 | 22 | 18 | 61 | 19 |
| Maxi = | 70 | 83 | 38 | 135 | 44 |
| SR | 0.16 | 0.19 | 0.11 | 0.11 | 0.12 |

TABLE 3

FERTILITY OF MICROPLATES MU/EC (SANOFI DIAGNOSTICS PASTEUR)

| Microplate batches | E. coli WR1/100 ml | Yield (%) | Control |
|---|---|---|---|
| 1 | 603 | 118 | Accepted |
| 2 | 633 | 124 | Accepted |
| 3 | 522 | 102 | Accepted |
| 4 | 471 | 92 | Accepted |
| 5 | 452 | 88 | Accepted |
| 6 | 325 | 64 | Refused |
| 7 | 371 | 73 | Accepted |
| 8 | 360 | 70 | Accepted |
| 9 | 817 | 160 | Refused |
| 10 | 742 | 145 | Accepted |
| 11 | 633 | 124 | Accepted |
| 12 | 479 | 94 | Accepted |
| 13 | 471 | 92 | Accepted |
| 14 | 409 | 80 | Accepted |
| 15 | 387 | 76 | Accepted |
| 16 | 381 | 75 | Accepted |
| 17 | 315 | 62 | Refused |
| 18 | 789 | 154 | Accepted |
| 19 | 772 | 151 | Accepted |
| 20 | 781 | 153 | Accepted |
| 21 | 518 | 101 | Accepted |

Target value 511

TABLE 4

FERTILITY OF MICROPLATES MU/SF (SANOFI DIAGNOSTICS PASTEUR)

| Microplate batches | E. faecalis CCM 2541/100 ml | Yield (%) | Control |
|---|---|---|---|
| 1 | 661 | 132 | Accepted |
| 2 | 601 | 120 | Accepted |
| 3 | 433 | 87 | Accepted |
| 4 | 507 | 102 | Accepted |
| 5 | 359 | 72 | Accepted |
| 6 | 327 | 66 | Accepted |
| 7 | 326 | 65 | Refused |
| 8 | 540 | 108 | Accepted |
| 9 | 592 | 119 | Accepted |
| 10 | 424 | 85 | Accepted |
| 11 | 441 | 88 | Accepted |
| 12 | 562 | 113 | Accepted |
| 13 | 570 | 114 | Accepted |
| 14 | 650 | 130 | Accepted |
| 15 | 602 | 121 | Accepted |
| 16 | 441 | 88 | Accepted |

TABLE 4-continued

FERTILITY OF MICROPLATES MU/SF (SANOFI DIAGNOSTICS PASTEUR)

| Microplate batches | E. faecalis CCM 2541/100 ml | Yield (%) | Control |
|---|---|---|---|
| 17 | 436 | 87 | Accepted |
| 18 | 595 | 119 | Accepted |
| 19 | 646 | 129 | Accepted |
| 20 | 592 | 119 | Accepted |
| 21 | 517 | 104 | Accepted |
| 22 | 434 | 87 | Accepted |
| 23 | 495 | 99 | Accepted |
| 24 | 526 | 105 | Accepted |
| 25 | 442 | 89 | Accepted |

Target value 499

TABLE 5

FERTILITY OF MICROPLATES MU/SF (SANOFI DIAGNOSTICS PASTEUR)

| Microplate batches | E. faecium WR63/100 ml | Yield (%) | Control |
|---|---|---|---|
| 1 | 746 | 105 | Accepted |
| 2 | 656 | 92 | Accepted |
| 3 | 626 | 88 | Accepted |
| 4 | 1031 | 145 | Accepted |
| 5 | 666 | 94 | Accepted |
| 6 | 518 | 73 | Accepted |
| 7 | 492 | 69 | Accepted |
| 8 | 660 | 93 | Accepted |
| 9 | 588 | 83 | Accepted |
| 10 | 611 | 86 | Accepted |
| 11 | 460 | 65 | Refused |
| 12 | 802 | 113 | Accepted |
| 13 | 990 | 139 | Accepted |
| 14 | 696 | 98 | Accepted |
| 15 | 742 | 104 | Accepted |
| 16 | 1147 | 161 | Refused |
| 17 | 915 | 129 | Accepted |
| 18 | 999 | 140 | Accepted |
| 19 | 750 | 105 | Accepted |
| 20 | 881 | 124 | Accepted |
| 21 | 694 | 98 | Accepted |
| 22 | 869 | 122 | Accepted |
| 23 | 662 | 93 | Accepted |
| 24 | 695 | 98 | Accepted |
| 25 | 434 | 61 | Refused |

Target value 711

TABLE 6

FERTILITY OF MICROPLATES MU/SF (SANOFI DIAGNOSTICS PASTEUR)

| Microplate batches | E. hirae CCM 2423/100 ml | Yield (%) | Control |
|---|---|---|---|
| 1 | 447 | 95 | Accepted |
| 2 | 457 | 97 | Accepted |
| 3 | 462 | 98 | Accepted |
| 4 | 493 | 104 | Accepted |
| 5 | 400 | 85 | Accepted |
| 6 | 376 | 80 | Accepted |
| 7 | 396 | 84 | Accepted |
| 8 | 475 | 101 | Accepted |
| 9 | 523 | 111 | Accepted |
| 10 | 436 | 92 | Accepted |
| 11 | 414 | 88 | Accepted |
| 12 | 568 | 120 | Accepted |
| 13 | 565 | 120 | Accepted |
| 14 | 575 | 122 | Accepted |
| 15 | 545 | 115 | Accepted |
| 16 | 498 | 105 | Accepted |
| 17 | 554 | 117 | Accepted |
| 18 | 410 | 87 | Accepted |
| 19 | 301 | 64 | Refused |
| 20 | 564 | 119 | Accepted |
| 21 | 584 | 124 | Accepted |
| 22 | 484 | 102 | Accepted |
| 23 | 544 | 115 | Accepted |
| 24 | 590 | 125 | Accepted |
| 25 | 329 | 70 | Accepted |

Target value 472

TABLE 7

| | In log of the number of bacteria in 100 ml: |  |  |
|---|---|---|---|
| $m^{(x)}$ | 1, 62, namely 42 bacteria in 100 ml | | |
| $S_u^{(x)}$ | 0.10 | | |
| $r^{(x)}$ | 0.18 | $CV_r\%$ | 4 |
| $R^{(x)}$ | 0.30 | $CV_R\%$ | 6.5 |
| $S_R^{(x)}/S_r$ | 1.5 | | |

What is claimed is:

1. A composition for forming a dry lens-shaped pellet comprising:
   about 20 to 40% by weight albumin and about 2 to 5% by weight starch,
   about 40 to 90% by weight sugar and/or salt,
   and about $10^2$ to $10^{11}$ microorganisms per gram of the composition.

2. The composition according to claim 1, wherein the sugar comprises saccharose in an amount of from about 60% to 80% by weight of the composition.

3. The composition according to claim 1, wherein the albumin is ovalbumin.

4. The composition according to claim 1, wherein the microorganisms are selected from the group consisting of bacteria, viruses, yeasts, protozoa, and fungi.

5. A pellet comprising the composition according to any one of claims 1, 2, 3 and 4.

6. The pellet according to claim 5, wherein the pellet has a mass in the range of from about 1 mg to about 250 mg.

7. The pellet according to claim 5, wherein the pellet is lens-shaped and has a diameter in the range of from about 1 mm to 10 mm.

8. A process for producing the pellet according to claim 5, comprising:
   mixing the microorganisms with the albumin and starch to form a mixture,
   reducing water activity of the mixture by progressively adding the sugar and/or salt to the mixture,
   shaping the mixture into pellets, and
   drying the pellets under vacuum and at a temperature lower than about −10° C.

9. The process according to claim 8, wherein the pellet drying is effected in a desiccator for a period of about 12 hours to about 10 days.

10. A process for producing a suspension of microorganisms from the pellet according to claim 9, or from the pellet obtained by the process according to claim 8, comprising resuspending the pellet into a suitable medium.

11. The process according to claim 10, wherein the pellet is resuspended in a liquid medium containing 23 g/l of salt.

12. A process comprising:

reconstituting the pellet according to claim 5; and comparing the reconstituted pellet to an experimental sample.

13. A process comprising:

reconstituting the pellet according to claim 5, in a culture medium to be tested; and ascertaining the level of growth of the microorganisms in the culture medium.

14. A process comprising:

placing the pellet according to claim 5, in a foodstuff to be tested;

storing the treated foodstuff under normal storage conditions for that foodstuff; and ascertaining the level of growth of the microorganisms in the foodstuff.

15. A process comprising:

incorporating into a fermentation material, the pellet according to claim 5 as a starting agent in a fermentation process; and fermenting the fermentation material.

16. The pellet according to claim 6, wherein the pellet has a mass of from about 2 to about 100 mg.

17. The pellet according to claim 6, wherein the pellet has a mass of from about 10 to about 25 mg.

18. Pellets for preserving microorganisms obtained by drying a composition comprising:

about 20 to 40% by weight albumin and about 2 to 5% by weight starch, about 40 to 90% by weight sugar and/or salt, and about $10^2$ to $10^{11}$ microorganisms per gram of the composition.

19. Pellets according to claim 18, wherein the sugar comprises saccharose which is from 60 to 80% by weight of the composition.

20. Pellets according to claim 18, wherein albumin is ovalbumin.

21. Pellets according to claim 18, wherein the microorganisms are bacteria, virus, yeasts, protozoa or fungi.

22. Pellets according to claim 18, wherein the mass of the pellet is in the range of from 1 mg to 250 mg.

23. Pellets according to claim 22, wherein the mass is in the range from 2 to 100 mg.

24. Pellets according to claim 23, wherein the mass is in the range from 10 to 25 mg.

25. Pellets according to claim 18, which are lens-shaped and have a diameter in the range from 1 to 10 mm.

26. Process for producing pellets according to claim 19, comprising:

mixing the albumin and microorganisms, adding the starch, adding the saccharose and then drying the pellets under vacuum and at a temperature lower than about −10° C.

27. Process according to claim 26, wherein the drying is effected in a desiccator for a period of about 12 hours to 10 days.

* * * * *

UNITED STATES PATENT AND TRADEMARK OFFICE
CERTIFICATE OF CORRECTION

PATENT NO.     : 6,723,526 B1
DATED          : April 20, 2004
INVENTOR(S)    : Jean-Francois Hernandez It is certified that error appears in the above-identified patent and that said Letters Patent is hereby corrected as shown below:

<u>Column 14,</u>
Line 34, "weight sugar" should read -- weight of sugar --.
Line 46, "1,2,3 and 4." should read -- 1,2,3, and 4. --.
Line 65, "claim 9," should read -- claim 5, --.

<u>Column 15,</u>
Lines 8 and 14, "claim 5, in" should read -- claim 5 in --.

<u>Column 16,</u>
Line 1, "weight albumin" should read -- weight of albumin --.
Line 3, "40 to 90%" should read -- 40 to 90 percent --.
Line 7, "saccharose which" should read -- saccharose, which --.

Signed and Sealed this

Eleventh Day of April, 2006

JON W. DUDAS
*Director of the United States Patent and Trademark Office*